United States Patent [19]

Schwartzman et al.

[11] Patent Number: 4,906,467

[45] Date of Patent: Mar. 6, 1990

[54] NOVEL, LONG-DURATION TREATMENT FOR GLAUCOMA

[75] Inventors: Michal L. Schwartzman, Elmsford; Michael W. Dunn, New Rochelle; Jaime L. Masferrer, Tarrytown, all of N.Y.

[73] Assignee: New York Medical College, Valhalla, N.Y.

[21] Appl. No.: 172,588

[22] Filed: Mar. 24, 1988

[51] Int. Cl.$^4$ .............................................. A61K 31/20
[52] U.S. Cl. ....................................... 424/80; 424/78; 514/560
[58] Field of Search ................................. 514/560, 913

[56] References Cited

U.S. PATENT DOCUMENTS

| | | | |
|---|---|---|---|
| 2,934,570 | 4/1960 | Goldberg et al. | 260/633 |
| 3,450,821 | 6/1969 | Carstensen et al. | 424/318 |
| 3,461,210 | 8/1969 | Fossel | 424/312 |
| 4,190,669 | 2/1980 | Voorhees et al. | 424/305 |
| 4,584,320 | 4/1986 | Rubin | 514/560 |

OTHER PUBLICATIONS

N. Abraham et al., "Presence of Heme Oxygenase and NADPH Cytochrome P$_{450}$ (c) Reductase in Human Corneal Epithelium," *Invest. Opthalmol. Vis. Sci.*, 28, pp. 1464–1472 (1987).

M. Schwartzman et al., "Cytochrome P$_{450}$ Dependent Metabolism of Arachidonic Acid in Bovine Corneal Epithelium," *Biochem. Biophys. Res. Comm.*, 132, pp. 343–351 (1985) (Schwartzman I).

M. Schwartzman et al., "Cytochrome P$_{450}$-Dependent Arachidonate Metabolism in Corneal Epithelium: Formation of Biologically Active Compounds," *Adv. Prostaglandin, Thrombox and Leuk. Res.*, 17, pp. 78–83 (1987) (Schwartzman II).

M. Schwartzman et al., "Cytochrome P450, Drug metabolizing Enzymes and Arachidonic Acid Metabolism in Bovine Ocular Tissues," *Current Eye Res.*, 6, pp. 623–630 (1987) (Schwartzman III).

M. Schwartzman et al., "Identification of Novel Cornea Arachidonic Acid Metabolites: Characterization of Their Biological Activities," abstract *Invest. Ophthalmol. Vis. Sci.*, vol. 28, Supp. 3, p. 328 (1987) (Schwartzman IV).

M. Schwartzman et al., "12(R)-HETE—A Cytochrome P$_{450}$-Dependent Arachidonate Metabolite That Inhibits Na$^+$-K$^+$-ATPase in the Cornea," *Proc. Natl. Acad. Sci.* (U.S.A.), vol. 84, pp. 8125–8129 (1987) (Schwartzman V).

M. Woolard, "Stereochemical Difference between 12-Hydroxy-5, 8, 10, 14-Eicosatetraenoic Acid in Platelets and Psoriatic Lesions," *Biochem. Biophys. Res. Comm.*, 136, pp. 169–176 (1986).

*Primary Examiner*—Douglas W. Robinson
*Attorney, Agent, or Firm*—Patricia A. Martone

[57] ABSTRACT

The present invention relates to a method of and composition for reducing intraocular pressure. The method comprises administering to a patient requiring such reduction of intraocular pressure a therapeutically effective amount of 12(R)-hydroxy-eicosa-5,8,10,14-tetraenoic acid (12(R)-HETE). The method of the present invention is particularly useful in treatment of all types of glaucoma. The method is also useful in lowering intraocular pressure in preparation for eye surgery, particularly for the removal of cataracts.

11 Claims, No Drawings

NOVEL, LONG-DURATION TREATMENT FOR GLAUCOMA

FIELD OF THE INVENTION

The present invention relates to a method of reducing intraocular pressure and a composition for use therewith. Said method comprises administering to a patient requiring such reduction of intraocular pressure a therapeutically effective amount of 12(R)-hydroxy-eicosa-5,8,10,14-tetraenoic acid (12(R)-HETE) or the pharmaceutically acceptable salts or esters thereof. The method and composition of the present invention are particularly useful in the treatment of glaucoma. They are also useful in lowering intraocular pressure in preparation for eye surgery, particularly for the removal of cataracts.

BACKGROUND OF THE INVENTION

Glaucoma is a disease complex characterized chiefly by an increase in intraocular pressure that, if sufficiently high and persistent, leads to damage to the optic nerve. This can cause irreversible blindness. Glaucoma is classed in three groups: primary, secondary and congenital.

Primary glaucoma is subdivided into angle closure and open angle types, based on the configuration of the angle of the anterior chamber of the eye where reabsorption of the aqueous humor occurs. [See generally Becker and Shaffer "Diagnosis and Therapy of the Glaucomas," C. V. Moslry Co., St. Louis (1976); A. G. Gilman et al. (eds.), *The Pharmacological Basis of Therapeutics*, Chapter 6, pp. 113–14, MacMillan Publishing Co., Inc., New York (6th ed. 1980).]

Angle closure glaucoma is nearly always a medical emergency in which drugs are essential in controlling the acute attack, but the long-range management is usually based predominantly on surgery (e.g., peripheral or complete iridectomy). Primary open angle glaucoma (POAG), on the other hand, has a gradual, insidious onset and usually responds to drug therapy. Certain cases, however, may require laser or surgical intervention in addition to drug treatment; failure of medical treatment necessitates surgery.

In POAG there is no visible obstruction or abnormality in the trabecular meshwork. Nevertheless, it is widely postulated that most of the resistance to the outflow of aqueous humor occurs here in the meshwork. In this circumstance, contraction of the ciliary muscle enhances tone and alignment of the trabecular network to improve resorption and outflow of aqueous humor through the network to the canal of Schlemm.

A large number of drugs have been used in the treatment of glaucoma. Andrenergic blocking agents, for example, are of great value in the management of the primary as well as of certain categories of the secondary type (e.g., aphakic glaucoma, following cataract extraction); the congenital type rarely responds to therapy other than surgical treatment. Each of these drugs, however, suffers from undesirable side effects or a need for frequent reapplication or instillation by sustained release. In contrast, the method of the present invention provides for a sustained and profound effect from occasional dosing. The method of the present invention is useful for treating the pressure elevation in all types of glaucoma.

Acute angle closure glaucoma may be precipitated by the injudicious use of a mydriatic agent in patients over 40, or by a variety of factors that can cause pupillary dilatation or engorgement of intraocular vessels [Gilman et al., supra, p. 113]. The cardinal signs and symptoms often include marked ocular inflammation, a semidilated pupil, severe pain and nausea. Every effort must be made to reduce the intraocular pressure to the normal level and maintain it there for the duration of the attack. In general, the most important drug for treatment is an osmotic agent such as oral glycerol to induce intraocular dehydration. Treatment adjuncts include beta blockers such as timolol and carbonic anhydrase inhibitors. Some physicians prefer a choinergic such as pilocarpine in early treatment. Laser iridotomy has recently been found to have an important role in the management of angle closure glaucoma. The long-acting organophosphorus compounds are not indicated in angle closure glaucoma because of vascular engorgement and an increase in the angle block.

POAG and secondary glaucoma require careful consideration of the needs of the individual patient in selecting the drug or combination of drugs to be employed. The choices available include (1) parasympathomimetic agents (e.g., pilocarpine nitrate, 0.5 to 4%); (2) anti-ChE agents that are short acting (e.g., physostigmine salicylate, 0.02 to 1%) and long acting (demecarium bromide, 0.125 to 0.25%; echothiophate, 0.03 to 0.25%; isofluorophate, 0.005 to 0.2%); and, paradoxically, (3) sympathomimetic agents (e.g., epinephrine, 1 to 2%; dipivalyl epinephrine (0.1%). Drugs of the last-mentioned class are often most effective when used in combinations with AChE inhibitors or cholinergic agonists. They reduce intraocular pressure by decreasing secretion of aqueous humor, and they prevent engorgement of small blood vessels. Timolol, an adrenergic antagonist, has also been found to be effective in reducing intraocular pressure. Timolol does not cause pupillary constriction but appears to act by reducing the production of aqueous humor. Timolol is long acting, and administration is at 12-hour intervals. Timolol has become very popular in the treatment of POAG because of its effectiveness and lack of side effects. Despite the convenience of less frequent administration and the high potency of long-acting anti-cholinesterase agents, their use entails a greater risk of development of lenticular opacities and untoward autonomic effects which limit their usefulness.

Methacholine, carbacol, pilocarpine and aceclidine are muscarinic agents which can be used to reduce intraocular pressure [Gilman et al., supra, Chapter 5, pp. 96–98]. Methacholine, in concentrations up to 20%, in combination with neostigmine bromide, 5%, instilled intraconjunctivally at frequent intervals, has been recommended for the emergency treatment of acute attacks of narrow-angle glaucoma. Carbachol has been used (0.25 to 3.0%) for chronic therapy of noncongestive, wide-angle glaucoma. Pilocarpine, when applied locally to the eye, causes pupillary constriction, spasm of accomodation, and a transitory rise in intraocular pressure, followed by a more persistent fall. Aceclidine (Glaucostat) is a synthetic compound which is approximately as effective as pilocarpine in reducing intraocular pressure in glaucoma.

Intraocular pressure may be effectively controlled without the stinging sensation an myopia experienced immediately after the application of pilocarpine solution by the use of a drug-delivery system called Ocusert which achieves a sustained release of pilocarpine (20 or 40 μg per hour) for at least 7 days. However, many patients find the foreign body uncomfortable and have difficulty with the insertion of the device, which explains its current limited usefulness.

Anti-cholinesterase (AChE) agents produce a fall in intraocular pressure in both types of primary glaucoma, chiefly by lowering the resistance to outflow of the aqueous humor. Effects on the volumes of the various intraocular vascular beds (e.g., those of the iris, ciliary body, etc.) and on the rate of secretion of the aqueous humor into the posterior chamber may contribute secondarily to the lowering of pressure, or conversely may produce a rise in pressure preceding the fall. In narrow-angle glaucoma, the aqueous outflow is facilitated by the freeing of the entrance to the trabecular space at the canal of Schlemm from blockade by the iris, as the result of the drug-induced contraction of the sphincter muscle of the iris. Use of anti-cholinesterase agents has been limited by their side effects which include formation of iris cysts, headaches and cataracts.

Timolol is a nonselective β-adrenergic antagonist [Gilman et al., supra, p. 195]. Timolol maleate (e.g., Timoptic, Merck, Sharpe & Dohme) is an ophthalmic preparation used for treatment of POAG aphakic glaucoma and secondary glaucoma. Timolo does not change the size of the pupil or the tone of the ciliary body, and it does not interfere with vision. The duration of beneficial effect is about 7 hours. The side effects are minimal, although systemic absorption of the drug can occur, leading to slowing of the heart, so the drug should be used with caution in individuals with asthma, heart block or heart failure.

Epinephrine (0.25 to 2%) or dipivalyl epinephrine (0.1%) are used to treat open angle glaucoma, reducing the intraocular pressure by their local vasoconstrictor actions, which decreases production of aqueous humor [Gilman et al., supra, p. 171].

It is thought that carbonic anhydrase may play a role in the formation of aqueous humor. The carbonic anhydrase inhibitor acetazolamide reduces the rate of aqueous humor formation, thereby lowering intraocular pressure in patients with glaucoma.

Ganglionic blocking agents can impair transmission in the ciliary ganglion, causing incomplete mydriasis and partial loss of accommodation.

The compound 12(R)-HETE was first identified as an arachidonic acid metabolite in skin lesions [M. Woolard "Stereochemical Difference between 12-Hydroxy-5,8,10,14-Eicosatetraenoic Acid in Platelets And Psoriatic Lesions," *Biochem. Biophys. Res. Comm.* 136, pp. 169-76 (1986)]. Recently Schwartzman, et al., have demonstrated that 12(R)-HETE is not a lipoxygenase derived metabolite but, rather, a cytochrome P$_{450}$-dependent metabolite of arachidonic acid produced, inter alia, in the bovine corneal epithelium. [Schwartzman et al., "12(R)-HETE - A Cytochrome P$_{450}$-Dependent Arachidonate Metabolite That Inhibits Na$^+$-K$^+$-ATPase in the Cornea," *Proc. Natl. Acad. Sci. (USA)*, Vol. 84, pp. 8125-29 (1987)].

Cytochrome P$_{450}$ has been observed in several eye tissues including cornea, ciliary body, retinal pigment, pigment epithelium, lens epithelium and retina [N. Abraham et al., "Presence of Heme Oxygenase And NADPH Cytochrome P$_{450}$(c) Reductase In Human Corneal Epithelium," *Invest. Opthalmol. Vis. Sci.*, 28, pp. 1464-72 (1987)]. In bovine tissues, the ciliary body is known to have the highest level of drug metabolizing enzymes (presumably among eye tissues). Enzyme activity in the bovine corneal epithelium is about half of that found in ciliary bodies. [Id.]

SUMMARY OF THE INVENTION

The present invention relates to a method of and composition for reducing intraocular pressure. The method comprises administering to a patient requiring such reduction of intraocular pressure a therapeutically effective amount of 12(R)-hydroxy-eicosa-5,8,10,14-tetraenoic acid (12(R)-HETE). The method of the present invention is particularly useful in treatment of all types of glaucoma. The method is also useful in lowering intraocular pressure in preparation for eye surgery, particularly for the removal of cataracts.

DETAILED DESCRIPTION OF THE INVENTION

Generally speaking, the present invention relates to a method of reducing intraocular pressure, which comprises administering to a patient requiring such reduction of intraocular pressure a therapeutically effective amount of 12(R)-hydroxy-eicosa-5,8,10,14-tetraenoic acid (12(R)-HETE). The present invention is also directed to pharmaceutical compositions useful in practicing this method.

It is a primary objective of the present invention to provide a composition and treatment for long term reduction of intraocular pressure with minimal toxicity or side effects.

It is a further objective of the present invention to provide a composition and treatment for the treatment of glaucoma, and other conditions requiring reduced intraocular pressure, by topical administration of a safe and effective substance.

Other objects and advantages of the present invention will be apparent from a further reading of the specification and of the appended claims.

The use of 12(R)-HETE in the present invention provides numerous advantages. One of the primary advantages of this compound is that it is normally found in the eye, so side effects are minimal. The compound has also been found to provide a decrease in intraocular pressure for a period of several days.

Additionally, 12(R)-HETE's ability to lower intraocular pressure may be enhanced by using it in conjunction with other pressure lowering compounds such as cholinergics (carbachol, pilocarpene) anti-ChEs (physostigmine, demecarium, echothiophate and isoflurophate), sympathomimetics, adrenergic antagonists, hyperosmotic agents and carbonic anhydrase inhibitors.

12(R)-HETE has been shown to be an inhibitor of Na$^+$-K$^+$-ATPases and has been found in the corneal epithelium of the eye [Schwartzman et al., "Cytochrome P$_{450}$ Dependent Metabolism Of Arachidonic Acid In Bovine Corneal Epithelium," *Biochem. Biophys. Res. Comm.*, 132, pp. 343-51 (1985); Schwartzman et al., "Cytochrome P$_{450}$-Dependent Archdonate Metabolism In Corneal Epithelium: Formation Of Biologically Active Compounds," *Adv. Prostaglandin, Thrombox. and Leuk. Res.*, 17, pp. 78-83 (1987)]. The effect of 12(S)-HETE and 12(R)-HETE has also been studied in ciliary body and corneal epithelial Na$^+$-K$^+$-ATPase and only the R isomer exhibits a significant inhibition of enzyme activity [Schwartzman et al., "12(R)-HETE - A Cytochrome P$_{450}$-Dependent Arachidonate Metabolite That Inhibits Na$^+$-K$^+$-ATPase in the Cornea," *Proc. Natl. Acad. Sci. (USA)*, Vol. 84, pp. 8125-29 (1987)]. Until now, however, 12(R)-HETE has never been known to have a significant effect on intraocular pressure.

Although the invention is not meant to be limited to any specific theory as to how 12(R)-HETE, when used according to this invention, achieves the desired effect, the following discussion is presented in the hope that it will help other investigators in this art and will aid in the research in this field. The invention is, of course, not limited to this theory.

12(R)-HETE has been shown to inhibit $Na^+$-$K^+$-ATPase isolated from the ciliary body and the corneal epithelium [Schwartzman et al., *Proc. Natl. Acad. Sci.*, supra]. $Na^+$-$K^+$-ATPase is also important in secretion of aqueous humor by the ciliary body. This secretion accounts for approximately one half of the flow of aqueous humor, so an inhibition of $Na^+$-$K^+$-ATPase can be expected to decrease aqueous humor flow which could contribute to decreased intraocular pressure. However, since $Na^+$-$K^+$-ATPase is found in several eye tissues, a $Na^+$-$K^+$-ATPase inhibitor is likely to present complex pharmacological reactions. A compound which inhibits $Na^+$-$K^+$-ATPase may have other effects as well, including undesirable side effects. For example, cardiac glycosides, such as ouabain, are known to inhibit $Na^+$-$K^+$-ATPases and to decrease intraocular pressure, but also cause severe side effects including keratitis and inflammation of the cornea.

12(R)-HETE is known to inhibit $Na^+$-$K^+$-ATPase in the corneal epithelium in vitro. The expected result of such inhibition is a decreased pumping of $Cl^-$ ion in the cornea with a concomitant decrease in water removal capacity. The net effect of this would be a swelling of the cornea and loss of clarity. It would be expected that the corneal thickness would approximately double if $Na^+$-$K^+$-ATPase was substantially inhibited. It was unexpectedly observed, however, that after topical administration of 12(R)-HETE in vivo, there was no increase in corneal thickness, no loss of clarity, and no other observable side effects.

It is also possible that there is some effect of 12(R)-HETE on the outflow of aqueous humor which, if the effect is increased outflow, could contribute to a reduction in intraocular pressure.

To learn more about the metabolism of 12(R)-HETE in the eye, $^{14}$C-labelled 12(R)-HETE was prepared using the method of Example 1. After topical administration of 1-($^{14}$C)-12(R)-HETE to a rabbit eye, the levels of 12(R)-HETE and its metabolites were measured in various parts of the eye. The highest levels were found in the cornea, ciliary bodies and trabecular meshwork. Because of the high concentration in the ciliary bodies and the known $Na^+$-$K^+$-ATPase inhibition of 12(R)-HETE, it is believed that the effect on intraocular pressure is primarily due to decreased production of aqueous humor, but the observation of 12(R)-HETE (or a metabolite) in the trabecular meshwork suggests that here may be some additional effect on humor outflow by a mechanism not yet understood.

The term "topical" as applied herein relates to the use of the active ingredient incorporated in a suitable pharmaceutical carrier, and applied to the eye for exertion of local action. Accordingly, such topical compositions include those pharmaceutically acceptable forms in which the compound is applied externally by direct contact with the eye to be treated. Conventional pharmaceutical forms for this purpose include eye drops, controlled release devices, aerosols, and ointments.

It is preferred in practicing the method of this invention to apply an effective dose of 12(R)-HETE in a suitable carrier topically to the eye. After such application, the intraocular pressure drops within a few minutes and remains depressed for several days.

In accordance with this invention, the free acid or any of the conventional organic or inorganic pharmaceutically acceptable salts of 12(R)-HETE can be utilized. These salts include the alkali metal salts such as the sodium and potassium salts, ammonium salts and alkaline earth metal salts, such as the calcium salts. Any of the pharmaceutically acceptable organic salts of 12(R)-HETE, such as the organic amine salts, can be utilized in accordance with this invention. Typical organic amines which form salts of 12(R)-HETE which can be utilized in accordance with this invention include ethyl amine, diethyl amine, triethyl amine, ethylenediamine, mono, di and tri-ethanol amines, ethyl diethanol amine, and butyl-monoethanol amine, p-tertiaryamylphenyl diethanol amine, galactamine and N-methyl glucamine, glucosamine, guanidine, etc.

Any of the lower alkyl esters containing from 1 to 7 carbon atoms of 12(R)-HETE can be utilized in this invention. Suitable esters of 12(R)-HETE include the methyl, ethyl, butyl and isopropyl esters thereof.

In general, in treating the patient, 12(R)-HETE or its esters or pharmaceutically acceptable salts can be utilized in a range of dosages depending upon the needs and requirements of the patient, as diagnosed by the attending physician. In determining a dosage, the amount of compound administered must be sufficient to reduce ocular pressure, yet not so much as to cause side effects. To date, no untoward side effects have been observed at doses up to 1 $\mu$g per eye. It is preferred in practicing this invention to use a dose of from 0.1 $\mu$g/eye to 0.5 $\mu$g/eye when using the free acid form of 12(R)-HETE. One skilled in the art will readily recognize how to adjust dosages of the salts or esters of 12(R)-HETE in order to cause a reduction in ocular pressure. The following examples are presented in order to illustrate one mode of practicing the present invention. These examples should not be construed to limit the invention in any way.

EXAMPLES

A. Preparation of 12(R)-HETE

Materials. Arachidonic acid was from NuCheck (Elysian, Minn.) and [1-$^{14}$C] arachidonic acid (56 $\mu$Ci/mmol) ($^{14}$C-AA) was obtained from Amersham (Chicago, Ill.). [5,6,8,9,11,12,14,15-$^3$H(N)]-Arachidonic acid (220 Ci/mmol) ($^3$H-AA) was obtained from New England Nuclear (Boston, Mass.). [5,6,8,9,11,12,14,15-$^2$H$_8$]- Arachidonic acid (D$_8$-AA) was a gift from Dr. Howard Sprecher, Ohio State University. NADPH, NADP and glucose 6-phosphate were obtained from Sigma Chemical Co. (St. Louis, Mo.). Glucose 6-phosphate dehydrogenase was purchased from Boerhinger Mannheim (Indianapolis, Ind.). Synthetic 12(S)-HETE and 12(R)-HETE were obtained from Biomol, Research Laboratories (Philadelphia, Pa.). Bis(trimethylsilyl)trifluoroacetamide (BSTFA) was obtained from Supelco (Bellefonte, Pa.). Diazald, which was used to prepare ethereal solutions of diazomethane, and 5% Rh/Al$_2$O$_3$ were obtained from Aldrich (Milwaukee, Wis.). All solvents were HPLC grade.

Preparation of corneal microsomes. Fresh bovine eyes were obtained from the local abattoir. They were collected within 10 min. after slaughtering and immediately immersed in an ice-chilled saline solution and brought to the laboratory on ice within 1-2 hrs. The eyes were washed twice with 0.9% saline and the corneal epithelium was gently scraped off into phosphate buffered saline, pH 7.4, and homogenized by using a glass tissue grinder operated at low speed. The homogenate was centrifuged at 500 × g for 10 min. and the supernatant was centrifuged at 10,000 × g for 20 min. The 10,000 × g supernatant was further centrifuged at 105,000 × g for 90 min. and the resulting microsomal pellet resuspended in PBS, pH 7.4.

Archidonate metabolism. The incubation mixture contained 3 mg microsomal protein, $^{14}$C-AA (7 μM) and an NADPH generating-system composed of glucose 6-phosphate (0.1 mM), NADP, (0.4 μM), and glucose 6-phosphate dehydrogenase (1 unit). The incubation was carried out for 30 min. at 37° C. In some experiments, corneal microsomes (3 mg protein/ml) were incubated with a mixture of $^{14}$C-arachidonic acid diluted with cold arachidonic acid (30,000 cpm/μg) and deuterated arachidonic acid ($D_8$-AA) in a ratio of 1:3 $D_8$:$D_0$. The incubations were carried out for 30 min. at 37° C. in the presence of an NADPH-generating system. The reaction was terminated by acidification to pH 4.0 and the arachidonate metabolites were extracted with ethyl acetate. Extraction efficiency was 60-70%. The final extract was resuspended in 200 μl methanol and arachidonate metabolites were separated by reverse-phase HPLC.

Pulse labeling experiment in epithelial cells. Intact corneal epithelial cells were isolated as described above and washed twice with PBS buffer, pH 7.4. Approximately 1-2×10$^7$ cells were incubated with [$^3$H]-AA (2 μCi, 220 Ci/mmol) for 5 min. at 37° C. The reaction was terminated by acidification, radio-labeled metabolites were extracted and separated by reverse-phase HPLC as described below.

Separation and purification of arachidonate metabolites. Reverse-phase HPLC was performed on a $C_{18}$ Microsorb column (250×4.6 mm, Rainin Instrument Co., Inc., Mass.) using a linear gradient of 1.25% /min. acetonitrile:water:acetic acid (50:50:0.1) to acetonitrile:acetic acid (100:0.1) at a flow rate of 1 ml/min. Radioactivity was monitored by a flow detector (Radiometric Instrument and Chemical Co., Inc., Tampa, Fla.) and fractions (0.5 ml) were collected.

Fractions containing a peak labelled, for convenience, compound C were pooled, evaporated and resuspended in methanol. Compound C has a retention time of 18.5 min. and has been thoroughly described previously. See M. L. Schwartzman et al., *Biochem, Biophys. Act* 132, pp. 343-51 (1985). Methylation was performed with freshly prepared ethereal solution of diazomethane. The methylated fraction was further purified by TLC on silica gel G (Analtech, N.J.) using a mixture of hexane:ethyl acetate (3:1) as the solvent system. The methylated compound was reextracted with methanol and subjected to further derivatization.

Preparation and measurement of Na$^+$-K$^+$-ATPase activity. Partially purified corneal epithelial Na$^+$-K$^+$-ATPase was prepared according to the method described by P. L. Jorgenson, *Methods in Enzymology* 32, pp. 277-90 (1974). Briefly, corneal epithelial microsomes were solubilized with sodium dodecylsulfate (SDS) as follows: microsomes (1.4 mg/ml) were incubated with SDS (0.56 mg/m) in the presence of 2 mM EDTA, 50 mM imidazole and 3 mM ATP, pH 7.5, for 45 min. at room temperature and continuous stirring. The solubilized microsomes were then applied on discontinuous density gradients and centrifuged at 60,000 rpm for 90 min.; the gradient consisted of three successive layers of sucrose 29.4%, 15% and 10% (w/v). The pellet was resuspended in 25 mM imidazole and 1 mM EDTA, pH 7.5, and stored at 20° C.

The activity of Na$^+$-K$^+$-ATPase was measured as the rate of release of inorganic phosphate in the presence of 30 mM histidine, 20 mM KCl, 30 mM NaCl, 3 mM MgCl$_2$ and 3 mM ATP, pH 7.5 [Jorgenson, supra]. After equilibration for 5 min. at 37° C., 10 μl of the enzyme preparation (1-5 μg protein) was added to 0.5 ml of reaction mixture. The reaction was allowed to proceed for 30 min. at 37° C. The compounds to be tested were dissolved in PBS buffer and added to the enzyme 10 min. prior to the addition of the reaction mixture. Ouabain was dissolved in distilled water. The reaction was terminated by the addition of 0.8 ml color reagent containing ammonium molybdate malachite green and sterox as described by O. A. Candia et al., *Biochim. Biophys. Acta* 602, pp. 389-400 (1980). After 1 min., 100 μl of 34% sodium citrate solution was added and mixed. The final solution was then read at 660 mm in a Beckman DB spectrophotometer. Al solutions were read against references containing the same concentration of ATP as the incubation tubes. Enzyme activity was expressed as μmol Pi released/h/mg protein.

Spectrometric analysis of Peak C. Gas chromatography/mass spectrometry was carried out on a Nermag 1010C GC/MS using either electron impact (70 eV) ionization conditions or chemical ionization with methane as reagent gas (0.1 torr) and measuring either positive or negative ions. Gas chromatographic separations were carried out on a 10 m capillary DB-1 column (20 μ, J & W Scientific, Rancho Cordova, Calif.). Helium was used as carrier gas at a flow rate of 50 cm/sec. The methyl ester trimethylsilyl ether derivatives of compound C with and without prior catalytic reduction were prepared as previously described for electron impact GC/MS [M. Van Rollins et al., *J. Lipid Res.* 25, pp. 507-17 (1984)]. These derivatives were also studied by positive ion chemical ionization. Electron capture negative ion chemical ionization mass spectrometry was used to analyze the pentafluorobenzyl ester trimethylsilyl ether derivative of compound C which was prepared essentially following the method of R. J. Strife and R. E. Murphy, *J. Chromatography* 305:3-12 (1984). Ultraviolet spectroscopy was carried out using a Hewlett-Packard Model 8452A photodiode array spectrophotometer (Palo Alto, Calif.) using 20% methanol/water as solvent.

B. Use of 12(R)-HETE

A solution of 12(R)-HETE was prepared by dissolving 50 μg 12(R)-HETE in 1 ml ethanol and diluting to give aliquots containing 0.5 or 1.0 μg 12(R)-HETE in each of several containers. These could be frozen at −78° C. with or without ethanol. Before use, aliquots were warmed, ethanol was removed (if necessary) and sterile phosphate buffered saline (PBS) was added to give a concentration of 0.01 mg 12(R)-HETE/ml PBS. Rabbits were treated by administering 10 to 50 μl of 12(R)-HETE in PBS topically to the each eye of a 1.5 kg rabbit. Control rabbits were treated with PBS alone. Intraocular pressure was measured on a conventional pneumotometer, using a sensor size appropriate for the eye to be measured.

The pressure in each eye of the rabbits was measured several times before beginning the experiment to establish a baseline. Pressure was measured again just after administration of the test compound, then every 30 minutes for 180 minutes, daily for six days, and again on days 9 and 11. As seen in Table 1, the pressure in test animals was significantly below the pressure in control animals at all times after administration of the test drug. Table 1 illustrates the mean and standard error of the pressure difference from baseline in six animals treated with 0.5 μg 12(R)-HETE (per eye) compared with three controls, only one of which was tested after the first day. It can be seen that a short onset, sustained pressure drop was obtained using the method and composition of this invention.

TABLE 1

EFFECT OF 12(R)-HETE ON RABBIT INTRAOCULAR PRESSURE

| Time | 12(R)-HETE | Control |
|---|---|---|
| Base | 0.0 ± 1.4[1] | 0.0 ± 0.5[2] |
| 0 min. | −0.6 ± 0.9 | −0.16 ± 1.3 |
| 30 | −3.5 ± 1.9 | 0.6 ± 0.6 |
| 60 | −5.6 ± 1.4 | −0.7 ± 0.2 |
| 90 | −5.6 ± 1.3 | −0.6 ± 0.7 |
| 120 | −7.2 ± 1.6 | −0.9 ± 1.6 |
| 150 | −4.7 ± 2.8 | 0.1 ± 0.6 |
| 180 | −4.1 ± 2.2 | −0.4 ± 0.28 |
| 2 days | −3.2 ± 2.1 | 0.3[3] |
| 3 | −4.2 ± 1.2 | −0.9 |
| 4 | −4.2 ± 1.0 | 1.3 |
| 5 | −5.2 ± 2.1 | 0.5 |
| 6 | −6.0 + 1.2 | −1.5 |
| 9 | −7.4 ± 1.7 | −2.5 |
| 11 | −2.9 ± 1.5 | −2.5 |

[1] mm Hg ± SEM, n = 6; difference from baseline (25.6 mm)
[2] n = 3; baseline = 24.6 mm
[3] n = 1

The teachings of the art cited hereinbefore is hereby incorporated by reference. While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto, rather than by the specific embodiments which have been presented hereinbefore by way of example.

We claim:

1. A method for reducing intraocular pressure, which comprises administering to the eye a therapeutically effective amount of 12(R)-hydroxy-eicosa-5,8,10,14-tetraenoic acid or a pharmaceutically acceptable salt or ester thereof.

2. The method according to claim 1 wherein the 12(R)-hydroxy-eicosa-5,8,10,14-tetraneoic acid is dissolved or suspended in a vehicle suitable for topical administration to the eye.

3. The method according to claim 2 wherein said vehicle is selected from the group consisting of methylcellulose, balanced salt solution, PVP, polyvinyl alcohol, hydroxyethyl cellulose, hydroxy-propylcellulose, hydroxypropyl methylcellulose, polyvinyl alcohol, boric acid, mineral oil, and povidone.

4. The method according to claim 1 wherein the effective amount of 12(R)-hydroxy-eicosa-5,8,10,14-tetraenoic acid is 0.1-1 μg/eye.

5. The method according to claim 1 wherein the effective amount of 12(R)-hydroxy-eicosa-5,8,10,14-tetraenoic acid is 0.2-0.5 μg/eye.

6. A composition for the treatment of glucoma or ocular hypertension, consisting essentially of a therapeutically effective amount of 12(R)-hydroxy-eicosa-5,8,10,14-tetraenoic acid or a pharmaceutically acceptable salt or ester thereof and a pharmaceutically acceptable vehicle.

7. A composition in accordance with claim 6 wherein said vehicle is suitable for topical administration to the eye.

8. A composition in accordance with claim 6 wherein said vehicle is selected from the group consisting of methylcellulose, balanced salt solution, PVP, polyvinyl alcohol, hydroxyethyl cellulose, hydroxy-propylcellulose, hydroxypropyl methylcellulose, polyvinyl alcohol, boric acid, mineral oil, and povidone.

9. A composition according to claim 6 wherein the concentration of 12(R)-hydroxy-eicosa-5,8,10,14-tetraenoic acid is 2-20 μg/ml.

10. A method for treating glaucoma or ocular hypertension which comprises administering to the eye a therapeutically effective amount of 12(R)-hydroxy-eicosa-5,8,10,14-tetraenoic acid or a pharmaceutically acceptable salt or ester thereof.

11. The method according to claim 1, wherein the therapeutically effective amount of 12(R)-hydroxy-eicosa-5,8,10,14-tetraenoic acid is from 0.1 μg/eye to 1.0 μg/eye.

* * * * *

UNITED STATES PATENT AND TRADEMARK OFFICE
CERTIFICATE OF CORRECTION

PATENT NO. : 4,906,467

DATED : March 6, 1990

INVENTOR(S) : Michal L. Schwartzman, Michael W. Dunn and Jaime L. Masferrer

It is certified that error appears in the above-identified patent and that said Letters Patent is hereby corrected as shown below:

At column 1, line 4, insert:

-- This invention was made with Government support under grant number EY 06513 awarded by the National Institutes of Health of the Department of Health and Human Services. The Government has certain rights in the invention. --

Signed and Sealed this

Eleventh Day of February, 1992

Attest:

HARRY F. MANBECK, JR.

Attesting Officer

Commissioner of Patents and Trademarks